United States Patent
Altmann et al.

(10) Patent No.: US 11,406,308 B2
(45) Date of Patent: Aug. 9, 2022

(54) VISUALIZATION AND RECORDATION SYSTEM INTERFACE WITH VIRTUAL GROUND FOR BIOMEDICAL SYSTEM AND METHODS

(71) Applicant: Biosense Webster (Israel) Ltd., Yokneam (IL)

(72) Inventors: Andres Claudio Altmann, Haifa (IL); Vadim Gliner, Haifa (IL); Israel Zilberman, Yokneam (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 0 days.

(21) Appl. No.: 16/928,614

(22) Filed: Jul. 14, 2020

(65) Prior Publication Data
US 2022/0015658 A1    Jan. 20, 2022

(51) Int. Cl.
*A61B 5/316* (2021.01)
*A61B 5/25* (2021.01)
*A61B 5/0245* (2006.01)

(52) U.S. Cl.
CPC ............ *A61B 5/316* (2021.01); *A61B 5/0245* (2013.01); *A61B 5/25* (2021.01)

(58) Field of Classification Search
CPC .......... A61B 5/316; A61B 5/25; A61B 5/0245
See application file for complete search history.

(56) References Cited

U.S. PATENT DOCUMENTS

| 10,148,282 B1* | 12/2018 | Govari | H03M 3/39 |
| 2002/0007198 A1 | 1/2002 | Haupert | |
| 2007/0055125 A1 | 3/2007 | Anderson | |
| 2008/0065006 A1 | 3/2008 | Roger | |
| 2009/0018458 A1* | 1/2009 | Cao | A61B 5/30 600/509 |
| 2018/0132749 A1* | 5/2018 | Govari | A61B 5/287 |
| 2018/0303362 A1 | 10/2018 | Koertge et al. | |

(Continued)

FOREIGN PATENT DOCUMENTS

EP     3451540 A1     3/2019

OTHER PUBLICATIONS

Extended European Search Report dated Dec. 3, 2021 for European Patent Application No. 21185233.0.

*Primary Examiner* — Catherine M Voorhees
*Assistant Examiner* — Roland Dinga
(74) *Attorney, Agent, or Firm* — Volpe Koenig

(57) ABSTRACT

Methods, apparatus, and systems for medical procedures are disclosed herein. For example, a plurality of analog sensor signals and an analog reference signal are received by an analog-to-digital converter to produce respective digitized versions of the analog sensor signals. The respective digitized versions of the analog sensor signals are digital filtered to produce respective filtered digitized versions of the analog sensor signals. The filtered digitized versions of the analog sensor signals are output to a visualization system to provide real time display thereof. The filtered digitized versions of the analog sensor signals are communicated to a digital-to-analog converter to produce an analog version of the filtered digitized versions of the analog sensor signals. The analog version of the filtered digitized versions of the analog sensor signals along with the analog reference signal are output to a recordation system to provide supplemental processing and storage thereof.

20 Claims, 2 Drawing Sheets

(56) References Cited

U.S. PATENT DOCUMENTS

| | | | |
|---|---|---|---|
| 2019/0099133 A1* | 4/2019 | Govari | A61B 5/316 |
| 2019/0307348 A1* | 10/2019 | Govari | A61B 5/339 |
| 2020/0397328 A1* | 12/2020 | Altmann | A61B 5/6852 |

* cited by examiner

VISUALIZATION AND RECORDATION SYSTEM INTERFACE WITH VIRTUAL GROUND FOR BIOMEDICAL SYSTEM AND METHODS

FIELD OF INVENTION

The present application provides systems, apparatuses, and methods for improving medical procedures.

BACKGROUND

Medical conditions such as cardiac arrhythmia (e.g., atrial fibrillation (AF)) are often diagnosed and treated via intra-body procedures. For example, electrical pulmonary vein isolation (PVI) from the left atrial (LA) body is performed using ablation for treating AF. Pulmonary vein isolation and many other minimally invasive catheterizations require visualization and mapping of an intra-body surface as well as the display and/or recording of various biometric parameters captured by a variety of sensors.

Visualization of intra-body structures can be performed by mapping propagation of activation waves such as by fluoroscopies, computerized tomography (CT) and magnetic resonance imaging (MRI), as well as other techniques. For surgical procedures, the display of real time catheter locations within intra-body structures and other biomedical data assists the physician in the performance on non-invasive medical procedures using catheters and the like. In addition to providing a relatively real time display system, a recordation system is commonly provided to selectively process and store biometric sensor data. An example of a system used to assist non-invasive surgical procedures is the Carto® system sold by Biosense Webster.

SUMMARY

Methods, apparatus, and systems for medical procedures are disclosed herein.

In one example, a method for facilitating visualization of biometric data in conjunction with recordation of such data is provided. A plurality of analog sensor signals and an analog reference signal are received by an analog-to-digital converter to produce respective digitized versions of the analog sensor signals. The respective digitized versions of the analog sensor signals are digital filtered to produce respective filtered digitized versions of the analog sensor signals. The filtered digitized versions of the analog sensor signals are output to a visualization system to provide real time display thereof. The filtered digitized versions of the analog sensor signals are communicated to a digital-to-analog converter to produce an analog version of the filtered digitized versions of the analog sensor signals. The analog version of the filtered digitized versions of the analog sensor signals along with the analog reference signal are output to a recordation system to provide supplemental processing and storage thereof.

As such, the initially received analog reference signal serves as a virtual ground for the analog version of the filtered digitized versions of the analog sensor signals that are communicated to the recordation system in lieu of a degraded analog reference from the digital-to-analog converter.

The example method can include receiving a plurality of digital sensor signals. In such case, the digital sensor signals are filtered to produce respective filtered versions of the digital sensor signals and are output along with the filtered digitized versions of the analog sensor signals to the visualization system to provide real time display thereof. The filtered versions of the digital sensor signals are also communicated to the digital-to-analog converter to produce an analog version of the filtered versions of the digital sensor signals. The analog version of the filtered versions of the digital sensor signals along with the analog version of the filtered digitized versions of the analog sensor signals is output to the recordation system.

The method may include receiving a plurality of analog or digital sensor signals from catheters, ultrasound transducers, location pads or other biometric sensors. The method may include receiving analog signals such as Wilson Central Terminal signals from limb electrodes for producing an electrocardiogram and receiving a right leg signal from a right leg electrode as the analog reference signal.

An example apparatus for facilitating visualization of biometric data in conjunction with recordation of such data includes an analog-to-digital converter, digital filtering circuitry, and a digital-to-analog converter. The analog-to-digital converter is configured to receive a plurality of analog sensor signals and an analog reference signal to produce respective digitized versions of the analog sensor signals. The digital filtering circuitry is configured to filter the respective digitized versions of the analog sensor signals to produce respective filtered digitized versions of the analog sensor signals. The digital filtering circuitry is further configured to output the filtered digitized versions of the analog sensor signals to a visualization system to provide real time display thereof. The digital filtering circuitry is further configured to communicate the filtered digitized versions of the analog sensor signals to the digital-to-analog converter. The digital-to-analog converter is configured to produce an analog version of the filtered digitized versions of the analog sensor signals. An analog signal output is provided to output the analog version of the filtered digitized versions of the analog sensor signals along with the analog reference signal to a recordation system to provide supplemental processing and storage thereof.

The example apparatus can be provided such that the digital filtering circuitry is configured to receive and filter digital sensor signals of digital sensors to produce respective filtered versions of the digital sensor signals. In such case, the digital filtering circuitry is configured to output the filtered versions of the digital sensor signals along with the filtered digitized versions of the analog sensor signals to the visualization system to provide real time display thereof. The digital filtering circuitry is also configured to communicate the filtered versions of the digital sensor signals to the digital-to-analog converter to produce an analog version of the filtered versions of the digital sensor signals. The digital-to-analog converter is then configured to output the analog version of the filtered versions of the digital sensor signals along with the analog version of the filtered digitized versions of the analog sensor signals to the recordation system.

The analog-to-digital converter and digital filtering circuitry can be configured to receive respective analog and digital biometric data signals from catheters, ultrasound transducers, location pads or other types of sensors. In particular, the analog-to-digital converter can be configured to receive Wilson Central Terminal signals from limb electrodes for producing an electrocardiogram and to receive as the analog reference signal a right leg signal from a right leg electrode.

BRIEF DESCRIPTION OF THE DRAWINGS

A more detailed understanding can be had from the following description, given by way of example in conjunction with the accompanying drawings.

DETAILED DESCRIPTION

According to implementations of the disclosed subject matter, apparatus and methods are provided for conducting non-invasive medical procedures such as by use of a catheter within a subject for medical procedures, diagnostics, mapping or other purposes. Essentially real time visualization of internal body structures and catheter disposition comprises sensing and collecting data, processing it into images reflecting the position of the catheter within the subject's body and displaying serial images on a video monitor so that a physician or other operator who is controlling the movement of the catheter can use the video images to assist in the moving or otherwise operating the distal end of the catheter. The same and/or additional sensing data is also collected and stored in a recordation system for use at a later time. Data from the recordation system can be retrieved and used by real time visualization system to provide context for real time catheter movement or other purposes.

In one example system, a real time visualization system is provided that utilizes digitized sensor data. A sensor data recording system is also provided which receives analog sensor data, including an analog version of digitized sensor data provided to the visualization system and may also receive direct analog signals, such as Wilson Central Terminal ("WCT") signals from limb electrodes for producing an electrocardiogram ("ECG"). Alternatively, the WCT signals can be digitized by the visualization system then re-converted to analog for transmission to the recordation system.

Conventionally, analog sensor signals are compared to a ground or other reference signal for processing. For example, WCT signals are conventionally compared to the signal received from a right leg ("RL") sensor as a ground. However, in the example system, where digitized sensor signals are re-converted into analog signals for transmission to the recordation system, the reference signal that is produced is degraded.

Since the recording system can be distanced from the visualization system and analog signals transmitted to the recordation system may pick up additional noise in transmission. The recording systems are also limited with the filtering capabilities relative to the state of the art today. In order to provide improved data recordation and compatibility between the digital data utilized by the visualization system and the data stored in the recordation system, an interface component is provided which passes an analog version of filtered digitized sensor data to the recordation system along with a virtual ground reference signal.

Figure 1:
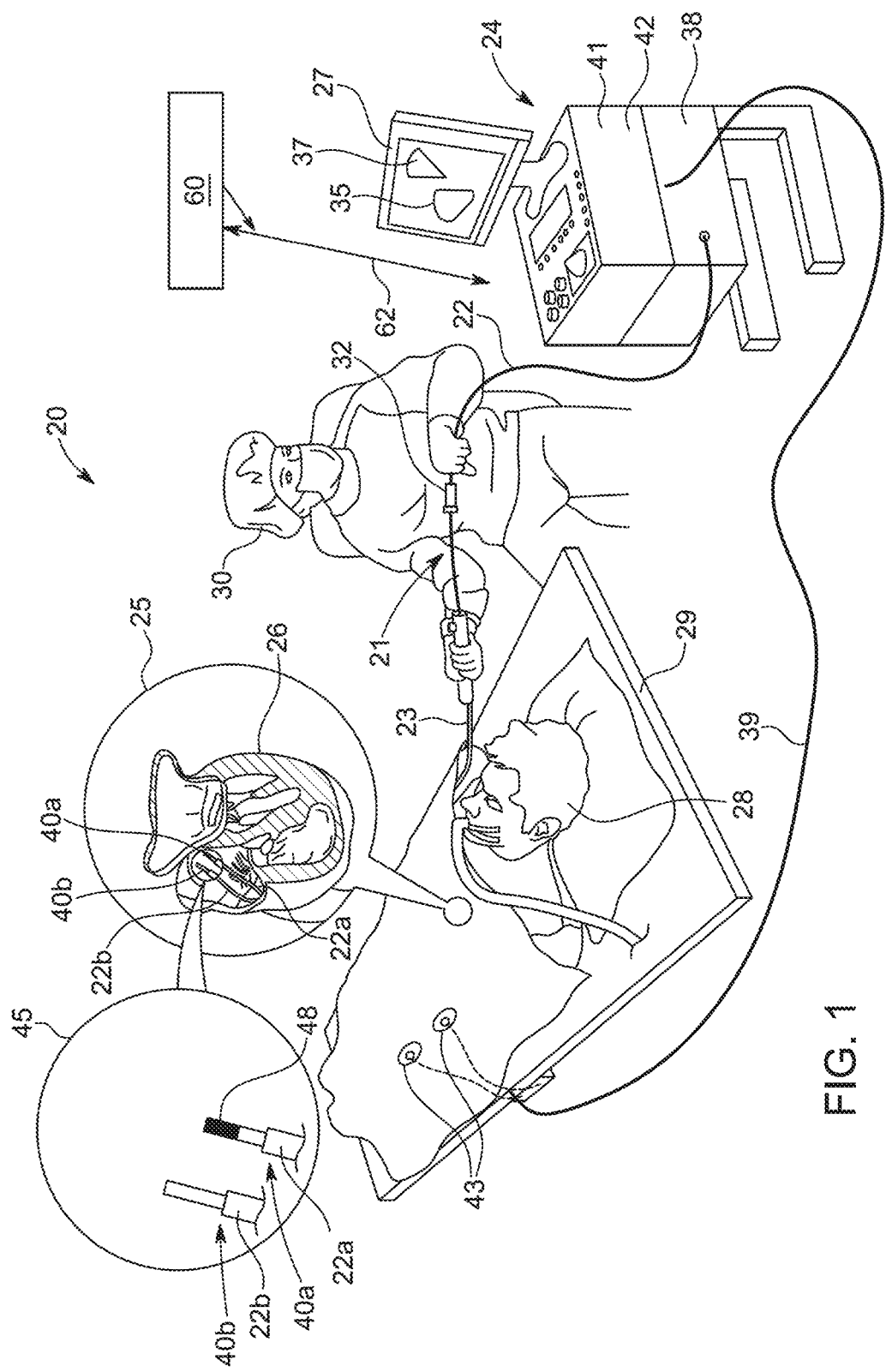
FIG. 1 is a diagram of an exemplary system in which one or more features of the disclosure subject matter can be implemented.

FIG. 1 is a diagram of an exemplary visualization system 20 in which one or more features of the disclosure subject matter may be implemented. Visualization system 20 may include devices, such as a catheter 40a and ultrasound transducer 40b (illustrated in inset 25), that are configured to obtain biometric data or ultrasound slices, in accordance with exemplary embodiments of the present invention. The example catheter 40a shown is a point catheter, it will be understood that other catheters may be used to implement the exemplary embodiments of the present invention. The example visualization system 20 includes a probe 21, having shafts 22a and 22b that may be navigated by a medical professional 30 into a body part, such as heart 26, of a patient 28 lying on a bed 29. According to exemplary embodiments of the present invention, multiple probes may be provided such that a first probe is in connection with the catheter 40a and a different probe is in connection with the ultrasound transducer 40b. However, for purposes of conciseness, a single probe 21 is described herein having a cable 22 for coupling probe signals to a processing interface 38, but it will be understood that probe 21 may represent multiple probes.

As shown in FIG. 1, a medical professional 30 may insert shaft 22a and/or 22b through a sheath 23, while manipulating the distal end of the shafts 22a and/or 22b using a manipulator 32 near the proximal end of the catheter 40a and/or ultrasound transducer 40b and/or deflection from the sheath 23. As shown in the inset 25, catheter 40a and/or ultrasound transducer 40b may be fitted at the distal end of shafts 22a and 22b respectively. Catheter 40a and/or ultrasound transducer 40b may be inserted through sheath 23 in a collapsed state and may be then expanded within heart 26.

According to exemplary embodiments of the present invention, ultrasound transducer 40b may be configured to obtain ultrasound slices of cardiac chamber of heart 26. Inset 45 shows the ultrasound transducer 40b in an enlarged view, inside a cardiac chamber of heart 26. As shown, ultrasound transducer 40b may be attached to shaft 22b.

According to exemplary embodiments of the present invention, catheter 40a may be configured to obtain biometric data of a cardiac chamber of heart 26. Inset 45 shows catheter 40a in an enlarged view, inside a cardiac chamber of heart 26. As shown, catheter 40 may include a point element 48 coupled onto the body of the catheter. According to other exemplary embodiments of the present invention, multiple elements may be connected via splines that form the shape of the catheter 40a. The element 48 may be any elements configured to obtain biometric data and may be electrodes, transducers, or one or more other elements.

According to exemplary embodiments of the present invention, biometric data may include one or more of LATs, electrical activity, topology, bipolar mapping, dominant frequency, impedance, or the like. The local activation time may be a point in time of a threshold activity corresponding to a local activation, calculated based on a normalized initial starting point. Electrical activity may be any applicable electrical signals that may be measured based on one or more thresholds and may be sensed and/or augmented based on signal to noise ratios and/or other filters. A topology may correspond to the physical structure of a body part or a portion of a body part and may correspond to changes in the physical structure relative to different parts of the body part or relative to different body parts. A dominant frequency may be a frequency or a range of frequencies that is/are prevalent at a portion of a body part and may be different in different portions of the same body part. For example, the dominant frequency of a pulmonary vein of a heart may be different than the dominant frequency of the right atrium of the same heart. Impedance may be the resistance measurement at a given area of a body part.

As shown in FIG. 1, the probe 21, ultrasound transducer 40b, and catheter 40a may be connected to a console 24. Console 24 may include a processor 41, such as a general-purpose computer, with suitable front end and interface circuitry 38 for transmitting and receiving signals to and from catheter 40*a* and ultrasound transducer 40*b*, as well as for controlling the other components of mapping system 20. Generally, interface circuitry 38 passes digital sensor data to the processor 41.

Some types of sensors output analog signals and other types of sensors output digital signals. The interface circuitry 38 is configured to receive biometric data from both types of sensors. For the various sensors that convey analog sensor data, the interface circuitry 38 includes appropriate analog-to-digital converters and digital filters to pass filtered digitized sensor data to the processor for visualization processing.

In some exemplary embodiments of the present invention, processor 41 is configured to generate rendering data for a global view and local view, based on the filtered digitized sensor data. According to exemplary embodiments of the present invention, the rendering data may be used to provide the medical professional 30 with a rendering of one or more body parts on a display 27, e.g., a body part rendering 35. According to an exemplary embodiment of the present invention, the processor may be external to the console 24 and may be located, for example, in the catheter, in an external device, in a mobile device, in a cloud-based device, or may be a standalone processor. According to exemplary embodiments of the present invention, the ultrasound transducer 40*b* may provide ultrasound slices which may be stored in memory 42, as further disclosed herein. The ultrasound transducer 40*b* may provide the ultrasound slices directly to memory 42 or the ultrasound slices may be provided to processor 41 and the processor 41 may provide the ultrasound slices to memory 42.

As noted above, processor 41 may include a general-purpose computer, which may be programmed in software to carry out the functions described herein. The software may be downloaded to the general-purpose computer in electronic form, over a network, for example, or it may, alternatively or additionally, be provided and/or stored on non-transitory tangible media, such as magnetic, optical, or electronic memory. The example configuration shown in FIG. 1 may be modified to implement the exemplary embodiments of the present invention. The disclosed exemplary embodiments of the present invention may similarly be applied using other system components and settings. Additionally, the visualization system 20 may include additional components, such as elements for sensing biometric patient data, wired or wireless connectors, processing and display devices, or the like.

According to an exemplary embodiment of the present invention, a display connected to a processor (e.g., processor 41) may be located at a remote location such as a separate hospital or in separate healthcare provider networks. Additionally, the visualization system 20 may be part of a surgical system that is configured to obtain anatomical and electrical measurements of a patient's organ, such as a heart, and performing a cardiac ablation procedure. An example of such a surgical system is the Carto® system sold by Biosense Webster.

The visualization system 20 may also, and optionally, obtain biometric data such as anatomical measurements of the patient's heart using ultrasound, computed tomography (CT), magnetic resonance imaging (MRI) or other medical imaging techniques known in the art. The visualization system 20 may obtain electrical measurements using catheters, electrocardiograms (EKGs) or other sensors that measure electrical properties of the heart. The biometric data including anatomical and electrical measurements may then be stored in a memory 42 of the visualization system 20, as shown in FIG. 1.

Control console 24 may be connected, by a cable 39, to body surface electrodes 43, which may include adhesive skin patches that are affixed to the patient 28. The processor, in conjunction with a current tracking module, may determine position coordinates of the catheter 40*a* and ultrasound transducer 40*b* inside the body part (e.g., heart 26) of a patient. The position coordinates may include the location and orientation of catheter 40*a* and ultrasound transducer 40*b*. The position coordinates may be based on impedances or electromagnetic fields measured between the body surface electrodes 43 and the electrode 48 or other electromagnetic components of the catheter 40*a*. Similarly, the position coordinates may be based on impedances or electromagnetic fields measured between the body surface electrodes 43 and the ultrasound transducer 40*b*. Additionally or alternatively, location pads may be located on the surface of bed 29 and may be separate from the bed 29. The position coordinates may be based on impedances or electromagnetic fields measured between the electrode 48 and/or a component of the ultrasound transducer 40*b*.

Control console 24 may also include an input/output (I/O) communications interface that enables the control console to transfer signals from, and/or transfer signals to electrode 48 and/or ultrasound transducer 40*b* and electrodes 43 or a location pad. Based on signals received from electrode 48, ultrasound transducer 40*b* and/or electrodes 43, processor 41 may generate rendering data that enables a display, such as display 27 to render a body part, such as a body part rendering 35.

During a procedure, processor 41 may facilitate the presentation of a body part rendering 35 and/or an ultrasound slice 37 to medical professional 30 on a display 27, and store data representing the body part rendering 35 and ultrasound slice 37 in a memory 42. Memory 42 may comprise any suitable volatile and/or non-volatile memory, such as random-access memory or a hard disk drive. In some exemplary embodiments of the present invention, medical professional 30 may be able to manipulate a body part rendering 35 and/or ultrasound slice 37 using one or more input devices such as a touch pad, a mouse, a keyboard, a gesture recognition apparatus, or the like. For example, an input device may be used to change the position of catheter 40*a* such that rendering 35 is updated and a different ultrasound slice 37 is provided based on the updated position, as disclosed herein. In alternative exemplary embodiments of the present invention, display 27 may include a touchscreen that can be configured to accept inputs from medical professional 30, in addition to presenting a body part rendering 35 and ultrasound 37, including a global view and a local view.

According to exemplary embodiments of the present invention, an ultrasound transducer may be configured to capture ultrasound slices at various positions within the intra-body organ. The ultrasound transducer may be the same as or similar to ultrasound transducer 40*b* of FIG. 1. The ultrasound transducer may be inserted into an intra-body organ, such as a heart 26 of FIG. 1. More specifically, the ultrasound transducer may be inserted into a chamber of in intra-body organ, such as a heart chamber of heart 26. The ultrasound transducer may be configured to automatically capture ultrasound slices at pre-determined intervals of time (e.g., one ultrasound slice per millisecond) or may be configured to capture ultrasound slices based on the position and/or movement of the ultrasound transducer. For example, the ultrasound transducer may be configured to capture up to a given number of ultrasound slices (e.g., three ultrasound slices) per each position of the ultrasound transducer. Accordingly, the ultrasound transducer may be configured to capture multiple ultrasound slices for each ultrasound transducer position. According to an exemplary embodiment of the present invention, a processor, such as processor 41 of FIG. 1, maybe configured to select a single ultrasound slice from a plurality of ultrasound slices at the same ultrasound position. The processor may select the single ultrasound slice based one or more factors such as ultrasound slice quality, ultrasound transducer stability while the ultrasound slice is collected, signal to noise ratio, or the like. As an example, an ultrasound slice quality may be determined based on the detected boundaries of the organ within the slice when compared to free space (e.g., a blood pool) of the organ within the slice. A first ultrasound slice may be replaced by a second ultrasound for the same ultrasound position, based on the selection and factors described herein.

As applied herein, an ultrasound position may correspond to either an ultrasound transducer position or an ultrasound slice position, as further described herein. An ultrasound transducer position may be the position of an ultrasound transducer when a given ultrasound slice is captured. The ultrasound transducer position may include an ultrasound transducer location (e.g., coordinates) and an ultrasound transducer orientation (e.g., angle), as further disclosed herein. The ultrasound slice position may correspond to the area, volume, or voxels occupied by the ultrasound slice. As applied herein, a catheter position may correspond to either a catheter location (e.g., coordinates) and orientation (e.g., angle) or may correspond to a catheter slice position, as further disclosed herein.

According to an exemplary embodiment of the present invention, an ultrasound transducer position or a catheter position may include both the location and orientation of the corresponding ultrasound transducer or catheter. A location (i.e., ultrasound transducer position or a catheter position) may be stored as or include coordinates which may be represented as Cartesian coordinates, polar coordinates, voxel coordinates, or any other applicable coordinates or a combination thereof. The location may be relative to a reference point which may be internal to the body, internal to an intra-body organ, internal to an intra-body organ chamber or external to the body. The location may be determined based on signals (e.g., electromagnetic signals) from the ultrasound transducer, the catheter, body surface electrodes (e.g., body surface electrodes 43 of FIG. 1), a location pad, or other location-based component.

An orientation may be based on a reference point (e.g., tip) of the ultrasound transducer or catheter such that the orientation indicates the direction that the reference point of the ultrasound transducer and/or catheter is facing. It will be understood that although a reference point is specifically recited herein, the reference point may be a collection of points, such as a line. The reference point may be any part of an ultrasound transducer or catheter such as a distal point, a proximal point, or any other applicable point. The orientation may be stored or include an angle, a phase, a direction, an axis, an elevation, or a combination thereof.

To supplement the visualization system 20, a recordation system 60 is provided. Digitized filtered sensor data transmitted to the processor 41 from the interface circuitry 38 is also passed to recordation system 60 in an analog form via a coupling 62. Preferably the coupling 62 is also configured to provide stored data from the recordation system 60 for use by the visualization system 20.

The coupling 62 may be a hard wired connection or via a network or other system generally known in the art such as an intranet, a local area network (LAN), a wide area network (WAN), a metropolitan area network (MAN), a direct connection or series of connections, a cellular telephone network, or any other network or medium capable of facilitating communication between the visualization system 20 and the recordation system 60. The coupling 62 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the coupling 62.

In some instances, the recordation system 60 may be implemented as a physical server. In other instances, the recordation system 60 may be implemented as a virtual server in a public cloud of computing provider (e.g., Amazon Web Services (AWS)®).

Figure 2:
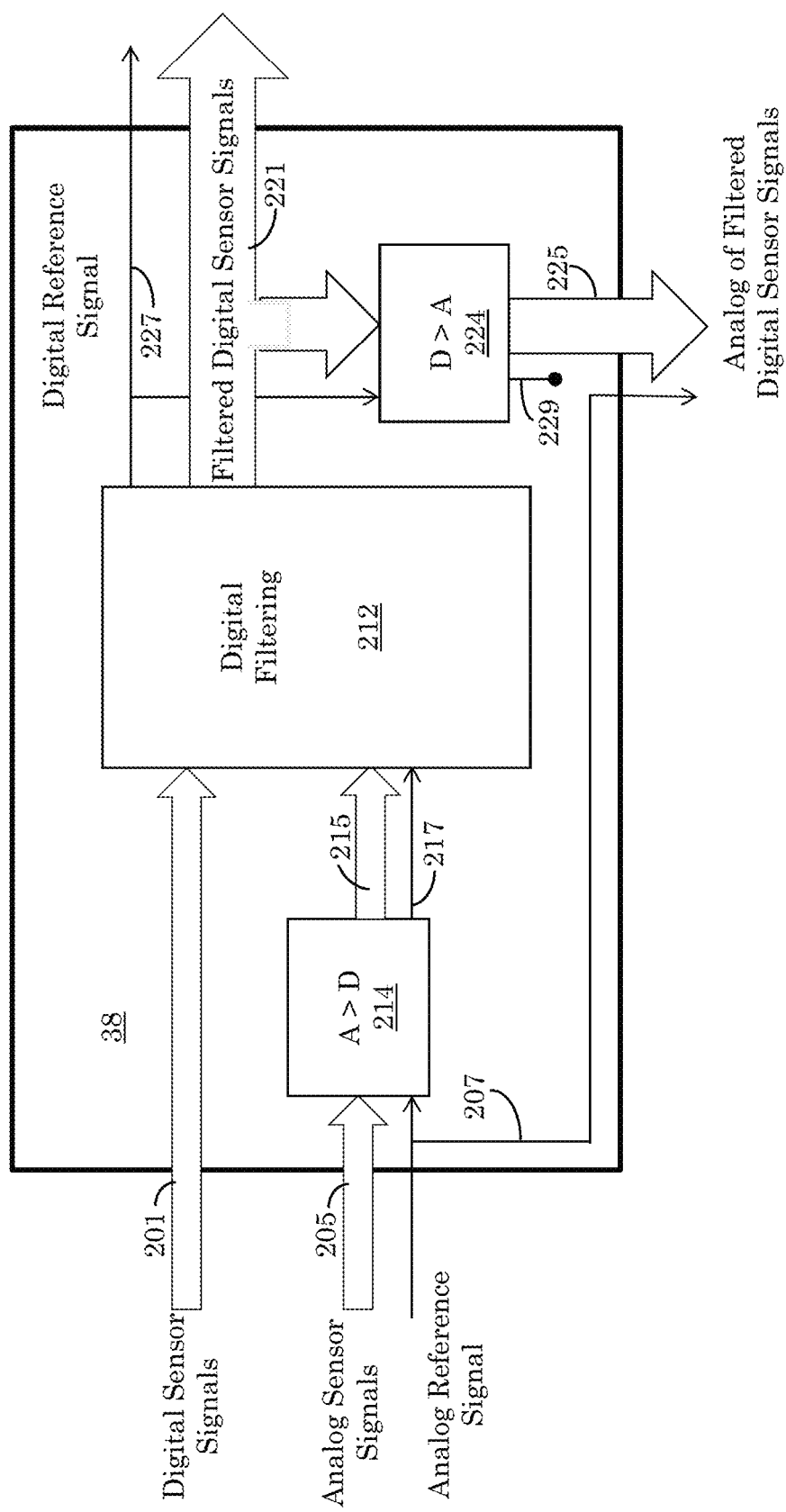
FIG. 2 is a schematic diagram of a portion of a data interface that processes sensor signals to output digital and analog version of filtered sensor signals.

With reference to FIG. 2, a more detailed example is provided of a portion of interface circuitry 38 which provides digital data output to processor 41 of the visualization system 20 and analog senor data output to the recordation system 60. The interface circuitry 38 includes a multi-lead digital sensor signal input 201, an analog sensor signal input 205, and an analog reference signal (or ground) lead 207. The interface circuitry 38 also includes a multi-lead digital sensor signal output 221, an analog sensor signal output 225, and a digital reference signal lead 227.

Digital signals from one or more sensors are input via respect leads of the digital sensor signal input 201 to a digital filtering component 212. The digital filtering component 212 may be implemented in hardware, software and/or a combination thereof. Analog signals from one or more sensors are input via respect leads of the analog sensor signal input 205 to an analog-to-digital converter 214. In one configuration, the analog signals include WTC signals for providing ECG data. An analog reference signal, such as a RL ground signal of a right leg surface electrode used in connection with WCT signals, is provided via the analog reference signal lead 207 to the analog-to-digital converter 214. With these inputs, the analog-to-digital converter 214 provides respective digitized sensor signals to the digital filtering component 212 via a multi-lead coupling 215 as well as a digitized reference signal to the digital filtering component 212 via a lead 217.

The digital filtering component 212 is configured to appropriately filter the respective digital signals derived from the various sensors based on the types of sensor from which each signal is received and to output respective filtered digital signals via the digital sensor signal output 221. These output signals from the digital filtering component 212 accordingly include filtered versions of the digital sensor signals along with the filtered digitized versions of the analog sensor signals input to the interface circuitry 38.

The digital sensor signal output 221 communicates the respective filtered digital signals to the processor 41 of the visualization system 20 and also inputs those signals to a digital-to-analog converter 224. The digital filtering component 212 also communicates the digital reference signal to the processor 41 of the visualization system 20 and also to the digital-to-analog converter 224 via the digital reference signal lead 227.

With these inputs, the digital-to-analog converter 224 provides analog versions of the filtered digital sensor signals from the interface circuitry 38 to the coupling 62 with the recordation system 60 via the analog sensor signal output 225. In conjunction with outputting the analog versions of the filtered digital sensor signals from the interface circuitry 38, the interface circuitry 38 outputs the analog reference signal via the analog reference signal lead 207 to the coupling 62 with the recordation system 60 thereby providing a virtual ground to the recordation signal.

An analog reference signal from a ground output 229 of the digital-to-analog converter 224 is not output from the interface circuitry 38. The analog reference signal received via lead 207 serves as a virtual ground for the analog version of the filtered digitized versions of the analog sensor signals that are communicated to the recordation system in lieu of a degraded analog reference from the digital-to-analog converter ground output 229.

Any of the functions and methods described herein can be implemented in a general-purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer-readable media). The results of such processing can be maskworks that are then used in a semiconductor manufacturing process to manufacture a processor which implements features of the disclosure.

Any of the functions and methods described herein can be implemented in a computer program, software, or firmware incorporated in a non-transitory computer-readable storage medium for execution by a general-purpose computer or a processor. Examples of non-transitory computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

It should be understood that many variations are possible based on the disclosure herein. Although features and elements are described above in particular combinations, each feature or element can be used alone without the other features and elements or in various combinations with or without other features and elements.

The invention claimed is:

1. A method for facilitating visualization of biometric data in conjunction with recordation of such data comprising:
   receiving a plurality of analog sensor signals by an analog-to-digital converter that uses an analog reference signal to produce respective digitized versions of the analog sensor signals;
   digital filtering the respective digitized versions of the analog sensor signals to produce respective filtered digitized versions of the analog sensor signals;
   outputting the filtered digitized versions of the analog sensor signals to a visualization system to provide real time display thereof;
   communicating the filtered digitized versions of the analog sensor signals to a digital-to-analog converter to produce an analog version of the filtered digitized versions of the analog sensor signals; and
   outputting the analog version of the filtered digitized versions of the analog sensor signals along with the analog reference signal used by the analog-to-digital converter to a recordation system to provide supplemental processing and storage of the biometric data.

2. The method of claim 1 wherein the receiving a plurality of analog sensor signals includes receiving Wilson Central Terminal signals from limb electrodes for producing an electrocardiogram.

3. The method of claim 2 wherein the receiving an analog reference signal includes receiving a right leg signal from a right leg electrode which signal is output to the recordation system.

4. The method of claim 2 wherein the receiving a plurality of analog sensor signals includes receiving biometric data signals from at least one of a catheter, an ultrasound transducer and a location pad.

5. The method of claim 1 further comprising:
   receiving a plurality of digital sensor signals;
   digital filtering the digital sensor signals to produce respective filtered versions of the digital sensor signals;
   outputting the filtered versions of the digital sensor signals along with the filtered digitized versions of the analog sensor signals to the visualization system to provide real time display thereof;
   communicating the filtered versions of the digital sensor signals to the digital-to-analog converter to produce an analog version of the filtered versions of the digital sensor signals; and
   outputting the analog version of the filtered versions of the digital sensor signals along with the analog version of the filtered digitized versions of the analog sensor signals to the recordation system.

6. The method of claim 5 wherein the receiving a plurality of digital sensor signals includes receiving biometric data signals from at least one of a catheter, an ultrasound transducer and a location pad.

7. The method of claim 6 wherein the receiving a plurality of analog sensors signal includes receiving Wilson Central Terminal signals from limb electrodes for producing an electrocardiogram.

8. The method of claim 7 wherein the receiving an analog reference signal includes receiving a right leg signal from a right leg electrode which signal is output to the recordation system.

9. The method of claim 6 wherein the receiving a plurality of analog sensor signals includes receiving biometric data signals from at least one of a catheter, an ultrasound transducer and a location pad.

10. The method of claim 9 wherein the receiving an analog reference signal includes receiving a right leg signal from a right leg electrode which signal is output to the recordation system.

11. An apparatus for facilitating visualization of biometric data in conjunction with recordation of such data comprising:
    an analog-to-digital converter configured to receive a plurality of analog sensor signals to produce respective digitized versions of the analog sensor signals using an analog reference signal;

digital filtering circuitry configured to filter the respective digitized versions of the analog sensor signals to produce respective filtered digitized versions of the analog sensor signals;

the digital filtering circuitry configured to output the filtered digitized versions of the analog sensor signals to a visualization system to provide real time display thereof;

the digital filtering circuitry configured to communicate the filtered digitized versions of the analog sensor signals to a digital-to-analog converter;

the digital-to-analog converter configured to produce an analog version of the filtered digitized versions of the analog sensor signals; and an analog signal output configured to output the analog version of the filtered digitized versions of the analog sensor signals along with the analog reference signal used by the analog-to-digital converter to a recordation system to provide supplemental processing and storage thereof.

12. The apparatus of claim 11 wherein the analog-to-digital converter is configured to receive Wilson Central Terminal signals from limb electrodes for producing an electrocardiogram.

13. The apparatus of claim 12 wherein the analog-to-digital converter is configured to receive as the analog reference signal a right leg signal from a right leg electrode which signal is output to the recordation system.

14. The apparatus of claim 12 wherein the analog-to-digital converter is configured to receive biometric data signals from at least one of a catheter, an ultrasound transducer and a location pad.

15. The apparatus of claim 11 wherein:
the digital filtering circuitry is configured to receive and filter digital sensor signals of digital sensors to produce respective filtered versions of the digital sensor signals;

the digital filtering circuitry is configured to output the filtered versions of the digital sensor signals along with the filtered digitized versions of the analog sensor signals to the visualization system to provide real time display thereof;

the digital filtering circuitry is configured to communicate the filtered versions of the digital sensor signals to the digital-to-analog converter to produce an analog version of the filtered versions of the digital sensor signals; and the digital-to-analog converter is configured to output the analog version of the filtered versions of the digital sensor signals along with the analog version of the filtered digitized versions of the analog sensor signals to the recordation system.

16. The apparatus of claim 15 wherein the digital filtering circuitry is configured to receive biometric data signals from at least one of a catheter, an ultrasound transducer and a location pad.

17. The apparatus of claim 16 wherein the analog-to-digital converter is configured to receive Wilson Central Terminal signals from limb electrodes for producing an electrocardiogram.

18. The apparatus of claim 17 wherein the analog-to-digital converter is configured to receive as the analog reference signal a right leg signal from a right leg electrode which signal is output to the recordation system.

19. The apparatus of claim 16 wherein the analog-to-digital converter is configured to receive biometric data signals from at least one of a catheter, an ultrasound transducer and a location pad.

20. The apparatus of claim 19 wherein the analog-to-digital converter is configured to receive as the analog reference signal a right leg signal from a right leg electrode which signal is output to the recordation system.

* * * * *